United States Patent
Schulz et al.

(10) Patent No.: US 8,787,648 B2
(45) Date of Patent: Jul. 22, 2014

(54) CT SURROGATE BY AUTO-SEGMENTATION OF MAGNETIC RESONANCE IMAGES

(75) Inventors: Heinrich Schulz, Hamburg (DE);
Michael Kaus, Madison, WI (US);
Vladimir Pekar, Toronto (CA);
Torbjoern Vik, Hamburg (DE)

(73) Assignee: Koninklijke Philips N.V., Eindhoven (NL)

(*) Notice: Subject to any disclaimer, the term of this patent is extended or adjusted under 35 U.S.C. 154(b) by 776 days.

(21) Appl. No.: 12/920,332

(22) PCT Filed: Feb. 25, 2009

(86) PCT No.: PCT/IB2009/050754
§ 371 (c)(1),
(2), (4) Date: Aug. 31, 2010

(87) PCT Pub. No.: WO2009/109874
PCT Pub. Date: Sep. 11, 2009

(65) Prior Publication Data
US 2011/0007959 A1    Jan. 13, 2011

Related U.S. Application Data

(60) Provisional application No. 61/034,535, filed on Mar. 7, 2008.

(51) Int. Cl.
*G06K 9/00* (2006.01)
*A61B 6/03* (2006.01)
*A61N 5/10* (2006.01)
*A61B 5/055* (2006.01)
*G06T 7/00* (2006.01)
*A61B 6/00* (2006.01)

(52) U.S. Cl.
CPC ............... *A61N 5/103* (2013.01); *A61B 6/4417* (2013.01); *A61B 6/037* (2013.01); *A61B 5/055* (2013.01); *G06T 7/0028* (2013.01); *A61B 6/032* (2013.01); *G06T 7/0038* (2013.01); *A61B 6/5247* (2013.01)
USPC ........................................... 382/132; 382/131

(58) Field of Classification Search
CPC ................ G06T 7/0038; G06T 7/0028; G06T 2207/10081; G06T 7/0083
USPC ........... 250/363.02, 363.04; 378/65; 606/130; 382/131, 132
See application file for complete search history.

(56) References Cited

U.S. PATENT DOCUMENTS 5,672,877 A * 9/1997 Liebig et al. ............. 250/363.04
6,368,331 B1 * 4/2002 Front et al. ...................... 606/130

(Continued)

OTHER PUBLICATIONS

Google Patents search, Jan. 31, 2013.*

(Continued)

*Primary Examiner* — Dilek B Cobanoglu

(57) ABSTRACT

When modeling anatomical structures in a patient for diagnosis or therapeutic planning, an atlas (26) of segmented co-registered CT and MRI anatomical structure reference images can be accessed, and an image of one or more such structures can be selected and overlaid with an MRI image of corresponding structure(s) in a clinical image of a patient. A user can click and drag landmarks or segment edges on the reference MRI image to deform the reference MRI image to align with the patient MRI image. Registration of a landmark in the patient MRI image to the reference MRI image also registers the patient MRI image landmark with a corresponding landmark in the co-registered reference CT image, and electron density information from the reference CT image landmark is automatically attributed to the corresponding registered patient MRI landmark.

18 Claims, 3 Drawing Sheets

(56) References Cited

U.S. PATENT DOCUMENTS

| | | |
|---|---|---|
| 7,292,037 B2 | 11/2007 | Vilsmeier et al. |
| 2006/0004284 A1 | 1/2006 | Grunschlager et al. |
| 2006/0237652 A1* | 10/2006 | Kimchy et al. .......... 250/363.02 |
| 2007/0263769 A1* | 11/2007 | Roell .............................. 378/65 |
| 2008/0039711 A1 | 2/2008 | Feilkas et al. |

OTHER PUBLICATIONS

The multimodality imaging challenge in radiotherapy (RT), Gilbert Boisserie, Radiotherapy Department of Pitie-Salpetriere Hospital, Paris, France, Aug. 26, 2003.*

Aribandi, M.; Limited MRI of the brain as an alternative to CT; 2006; The Lancet; 368:365-366.

Hadjiev, J., et al.; Application of MRI for improved local control in complex radiotherapy of cervical cancer; 2006; Arch Oncol; 14(3-4)95-100.

Kagadis, G. C., et al.; A comparative study of surface-and volume-based techniques for the automatic registration between CT and SPECT brain images; 2002; Med. Phys.; 29(2)201-213.

Khoo, V. S., et al.; Magnetic resonance imaging (MRI): considerations and applications in radiotherapy treatment planning; 1997; Radiotherapy and Oncology; 42:1-15.

Lagendijk, J.J.W., et al.; MRI/Linac integration; 2008; Radiotherapy and Oncology; 86:25-29.

* cited by examiner

CT SURROGATE BY AUTO-SEGMENTATION OF MAGNETIC RESONANCE IMAGES

CROSS REFERENCE TO RELATED APPLICATIONS

This application claims the benefit of U.S. provisional application Ser. No. 61/034,535 filed Mar. 7, 2008, which is incorporated herein by reference.

The present application finds particular utility in medical imaging systems. However, it will be appreciated that the described technique(s) may also find application in other types of imaging systems, therapy planning systems, and/or other medical applications.

For radiation treatment planning, combined magnetic resonance (MR)/positron emission tomography (PET), and other applications, the MR imaging modality is superior to computed tomography (CT) due to its better soft tissue discrimination. Unlike CT images that have an absolute scale, i.e., the Hounsfield Scale, there is no absolute scale for MRI images. This renders it difficult and inaccurate to use MR images instead of CT images.

The Hounsfield value measured with CT provides information necessary for, e.g., image-based dose calculation in radiation therapy planning (RTP) and attenuation correction for PET. With MRI-based RTP and MR/PET systems, CT and thus measured Hounsfield units are not available. This creates a need for a mechanism to estimate absorption coefficients or stopping power directly from MRI.

There is an unmet need in the art for systems and methods that facilitate overcoming the deficiencies noted above.

In accordance with one aspect, a system that provides electron density information in a magnetic resonance image (MRI) volume, includes a memory that stores an atlas (26) including a reference computed tomography (CT) image and a reference MRI image that are co-registered to each other, a display that presents a view of a patient MRI image and the reference MRI image, and a processor that executes an algorithm for associating electron density information from a corresponding landmark in the reference CT image with the selected landmark in the patient MRI image.

In accordance with another aspect, a method of providing electron density information for voxels in a magnetic resonance imaging (MRI) image includes generating generic co-registered computed tomography (CT) and MRI reference images from a plurality of respective CT and MRI images of a region of interest, receiving a patient MRI image, and registering the patient MRI image and the reference MRI image. The method further includes retrieving electron density information from corresponding segments of the co-registered CT image for the registered patient MRI image, and associating the retrieved electron density information with the registered patient MRI image.

According to another aspect, an atlas of co-registered computed tomography (CT) and magnetic resonance imaging (MRI) reference images of anatomical structures includes a plurality of CT and MRI reference images of anatomical structures, generated from scanned images of anatomical structures of one or more subjects, wherein the reference images are co-registered to associate electron density information from voxels in the CT reference images to corresponding voxels in respective MRI reference images. The atlas further includes a machine-readable medium that stores the plurality of co-registered CT and MRI reference images for recall and manipulation by an operator.

One advantage is that CT electron density information is transferred to a reference MRI image volume.

Another advantage resides in mapping spatial value information onto an MRI image.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

FIG. 1 illustrates a system for generating CT-specific information from images taken by magnetic resonance imaging devices to facilitate attenuation correction for upcoming PET/MR scans, dose calculations for radiation treatment on MR images, and the like.

Figure 1:
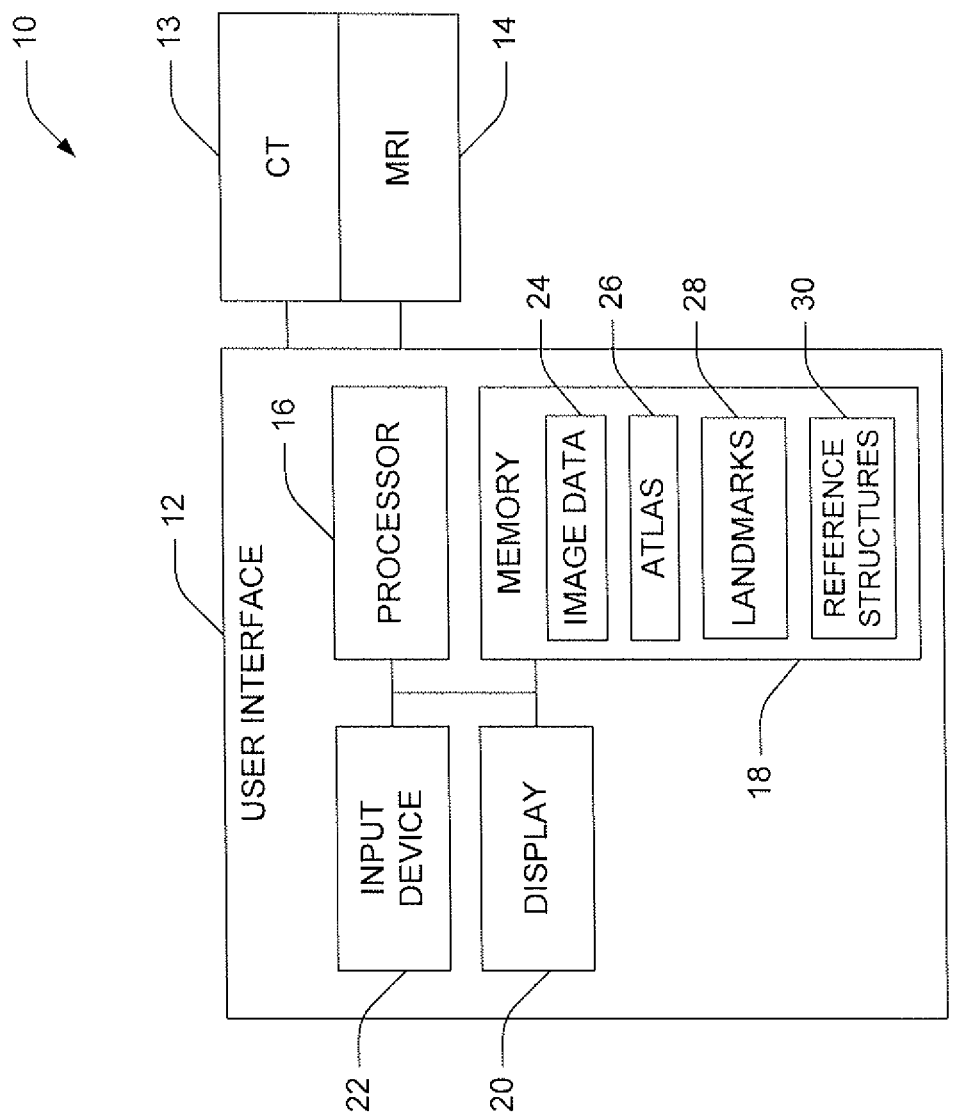

FIG. 1 illustrates a system 10 for generating CT-specific information from images taken by magnetic resonance imaging devices to facilitate attenuation correction for upcoming PET/MR scans, dose calculations for radiation treatment on MR images, and the like. The system 10 employs an algorithm to derive CT-specific information from MRI data sets, and includes a user interface 12 that is coupled to a CT scanner 13 and an MRI device 14. The MRI device may be a conventional MRI device, an integrated linear accelerated MRI (ILAMRI) device, or the like. In one embodiment, a combined CT-MRI imaging device is used. The user interface includes a processor 16 that executes algorithms and/or routines stored in a memory 18 for performing the various functions described herein. The user interface additionally includes a display 20 for presenting information to a user and an input device 22 (e.g., a mouse, stylus, keyboard, microphone, or other input device). The memory 18 includes image data 24 (e.g., collected by the CT and/or MRI devices), one or more atlases 26, a landmark database 28, and a reference structure database 30. The atlas comprises universal co-registered CT and MRI data from a plurality of subjects, deformed to converge to a common universal mapping of anatomical features. The landmark database comprises a plurality of landmarks common to the anatomical structures, which are used to permit an operator to manually deform (e.g., click and drag, etc.) a reference structure from the database 30 to a region of interest or structure in a patient image.

In one embodiment, the atlas 26 is populated by taking a number of CT and MRI images of different patients or subjects having different shapes and sizes, and manually registering landmarks for each. When a new patient is imaged using MRI for clinical assessment (e.g., diagnosis, therapy planning, radiation dose evaluation, etc.), the generic or universal MRI reference image is overlaid on the new patient MRI image and displayed on the display 20. An operator aligns corresponding landmarks to deformably register the new patient MRI image to the reference MRI image. Because the MR and CT reference images were previously registered to each other, registering the new MR image to the reference MR image also registers the new MR image to the reference CT image. The reference CT image is accessed to select Hounsfield values associated with corresponding landmarks, structures, or regions in the CT image and attribute them to voxels in the new patient MRI image. In this manner, CT intensity information is provided to an MRI patient image.

The processor 16 generates an atlas of a region to be examined in a patient. To generate the atlas 26, CT images and MR images of the region of interest in a variety of patients are generated by the CT scanner 13 and the MRI device 14. These images are both segmented (e.g., manually) to determine corresponding regions of like tissue in the CT and MRI portions of the atlas. During radiation treatment planning, an MRI image of the region of interest in a current patient is generated. The processor registers the patient MRI image with the atlas MRI image using an elastic transform. Registering the patient MRI image with the MRI atlas image also registers the patient MRI image with the CT atlas image. Based on this registration, corresponding CT or Hounsfield values are selected for each voxel of the patient MRI image for use in dose and other planning calculations. Alternately, a single CT value can be assigned to each of the segments and all voxels within a segment of the patient MRI image are correlated to the same CT or Hounsfield value.

In radiation planning, a series of trajectories through a target region (e.g., a tumor or the like) are selected. The shape, intensity, and dwell time of a treatment beam are also selected for each trajectory. The selection is performed to deliver a desired minimum radiation dose to the target region while not exceeding a maximum acceptable dose to surrounding tissue. The maximum acceptable dose varies with tissue type.

As the treatment beam travels to the target, it passes through tissue that attenuates the beam. Attenuation is a function of the Hounsfield or CY number, and is taken into account when calculating the dose delivered to the target. If there is patient motion during a treatment session, the tissue through which the beam passes on the way to the target can change. On-the-fly calculations are made to adjust the treatment protocol to be sure the minimum cumulative dose is delivered to the target without exceeding the maximums in other tissues.

The system 10 can be used not only in radiation treatment planning, but also during radiation treatment to monitor movement, or misregistration between the patient and the treatment beam. Based on a sensed misregistration, the treatment protocol can be modified or, if the patient moves too far, the treatment beam can be gated off.

In combined PET/MRI scanning, it is also advantageous to know the Hounsfield number for each voxel of the imaged region. Based on the Hounsfield number, a PET radiation attenuation correction can be made. With the described MRI/CT atlas, the electron density or Hounsfield number of each voxel can be determined from the MRI image for use in attenuation correction of the PET or SPECT imaging technique.

According to an example, a user deforms an anatomical atlas, including a 3D CT data set and a set of anatomical reference structures 30 and anatomical landmarks 28, to match individual patient MRI data sets. The deformation process provides a mapping of CT Hounsfield units from the atlas to the patient MRI data set. The atlas-based deformation can automatically determine an optimal scanplane from MRI scouts.

In one embodiment, the atlas of anatomical structures is created from a set of manually segmented image datasets of the targeted imaging modality MR taken from different patients. The segmentation consists of delineations of the anatomical structures of interest as well as of salient anatomical landmarks. The spatial variation of the delineations and the landmarks across the patient population is encoded in statistical models, e.g. by means of point distribution models.

A user or technician places salient landmarks by inspection of the gray values of the images. That is, the surrounding image information is characteristic for a given landmark. Therefore, a model of the surrounding image information accompanies the model of the spatial distribution of the landmarks. Landmarks correspond in a one to one relation across the training data, and by means of elastic image registration, the processor 16 warps all training images towards a common gray value image. This atlas image then contains the characteristic gray value image information in the neighborhood of each landmark.

The processor 16 performs the delineation of the same anatomical structures for respective CT images as well. Training images (e.g., MRI, CT, etc.) may be taken from different patients. From this data, a mapping of radio density to spatial regions/anatomical structures is generated by the processor. Multiple datasets are not mandatory due to the absolute Hounsfield scale of CT; nevertheless, the multiple data sets may be used to verify consistency of radio density values for delineated regions across different patients.

In another embodiment, rather than using the mapped Hounsfield values directly, the processor uses the deformed atlas to derive a coarse segmentation of the MRI data to derive grey value tissue models.

According to another embodiment, the system is employed in a combined MR-PET medical scanner (not shown). When the processor 16 receives patient MR data from the combined scanner, salient landmarks defined on the training data are retrieved. For instance, the processor can employ standard image processing techniques and make use of the gray value characteristics in the atlas image. To further facilitate identifying the spatial position and/or orientation of the region of interest in the patient image, the search space based on the statistical variation model of the spatial positions may be limited. After the landmarks are positioned, the delineated structures can be propagated from the MR reference data to the patient MR image. This is done with the same point-correspondence-based elastic approach as is used to generate the gray-value Hounsfield reference image. Radio (e.g., electron) density values are then assigned to regions in the patient MR image based on the stored mapping of radio density values to anatomical regions. Given the MR imaged labeled with radio density values, proper attenuation correction of a corresponding PET image can be performed.

In another embodiment involving radio therapy treatment planning systems a similar protocol is employed in the absence of an accompanying PET image. The resulting radio density-labeled MR image is used for dose calculation of the treatment planning system and omits the need for a CT image to execute a desired task.

Figure 2:
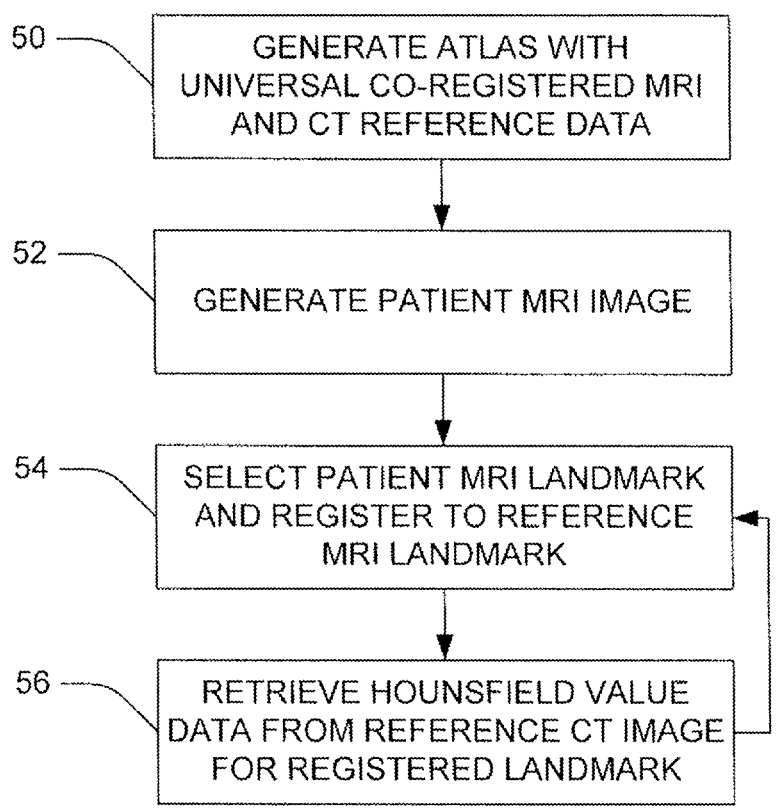
FIG. 2 illustrates a method for generating CT-specific information from images generated by an MRI device.

FIG. 2 illustrates a method for generating CT-specific information from images generated by an MRI device. At 50, an atlas of reference images is generated from CT and MRI scans of a plurality of subjects and/or regions of interest thereof. From this population, a universal or generic reference CT image volume and a universal or generic reference MRI image volume are constructed. The CT reference image has Hounsfield values associated with voxels, landmarks, structures and/or regions therein. The CT and MRI reference images are co-registered to each other, so that registration of a new MRI image to the reference MRI image also automatically registers the new MRI image to the CT reference image.

At 52, a patient MRI image volume is generated. At 54, a patient MRI image landmark is registered (e.g., automatically or manually) to a corresponding landmark in the reference MRI image. At 56, electron density information is retrieved from the co-registered reference CT image landmark and/or region and attributed to corresponding registered patient MRI image landmark and/or region. The electron density information can then be employed to perform attenuation correction on a subsequent MR/PET or MR/SPECT patient images. For example, Hounsfield unit value(s) for the selected registered MR reference image landmark can retrieved from the co-registered CT reference image landmark and attributed to the patient MRI image landmark. The method then reverts to 54 for further iterations of patient MRI image landmark selection and registration, and proceeds until a predefined or sufficient number of patient MRI image landmarks have been registered to perform a desired task (e.g., therapy planning, radiation dose calculation, attenuation correction, etc.).

Figure 3:
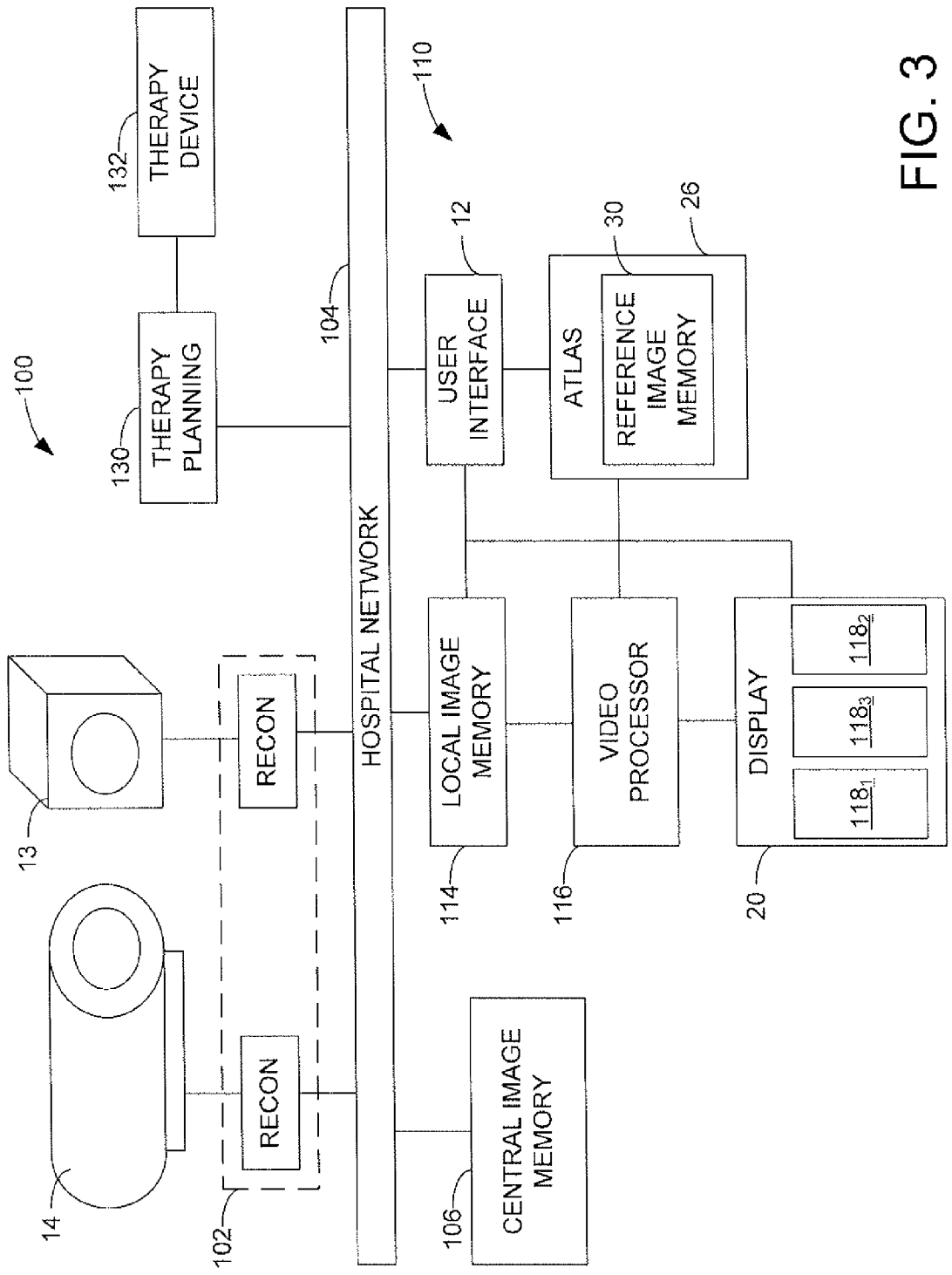
FIG. 3 illustrates an exemplary hospital system that includes a plurality of imaging devices, such as CT, MRI or the like, which generate imaging data that are reconstructed by individual or shared reconstruction processors to generate 3D image representations.

With reference to FIG. 3, an exemplary hospital system may include a plurality of imaging devices 100, such as CT 13, MRI 14, or the like, which generate imaging data that are reconstructed by individual or shared reconstruction processors 102 to generate 3D image representations. The image representations are communicated over a network 104 to a central memory 106.

At a station 110 connected with the network, an operator uses user interface 12 to move a selected 3D patient MRI image representation from the central memory to a local memory 114. A video processor 116 selects, for example, a reference image from the reference image memory 30 in the atlas 26 of reference images for display in a first viewport 118$_1$, of the display 20. The reference image can be selected manually by the operator, semi-automatically, or automatically. When selected semi-automatically, the operator is presented with a subset of reference images, automatically selected from a larger set of reference images, that closely match the size, identity, and/or shape of the organ(s) or tissue in the region of interest, and selects from the subset. When automatically selected, the processor 116 automatically selects a best-fit reference image that matches predefined criteria (e.g., size, shape, identity, etc., of the organ(s) or tissue in the region of interest in the patient image).

The patient MRI image is displayed in a second viewport 118$_2$. A third view port 118$_3$ can display a an overlay of the reference image and the patient image, to permit a user to register landmarks in the reference image to corresponding structures or landmarks in the patient image. For instance, the operator, through the interface 12, selects the patient image landmarks (e.g., using a mouse, stylus, or other suitable user input device) that correspond to landmarks in the reference image. The video processor then attributes electron density voxel values from the reference image to the patient image, to improve segmentation of the patient image.

In one embodiment, different types of tissue have different voxel values (e.g., "1" for bone, "2" for fatty tissue, and so on), and each voxel value is associated with an electron density. Registration of the patient image to the reference image associates voxel values with the patient image, thereby facilitating density estimation for structures in the patient image.

In another embodiment, the operator uses the user interface to select a reference image from the atlas 26, and the video processor superimposes the reference image on the patient MRI image in viewport 118$_3$. To conform the reference image to the shape of one or more of the structures in the patient image, the operator uses an input device to select a landmark on one or more segments of the patient image. The operator then designates a second landmark on the reference image as corresponding to the landmark on the patient image. CT data associated with the reference image landmark is then attributed to the patient MRI image landmark.

Once a sufficient number of landmarks have been registered, the patient image can be stored in the central memory 106 or used directly in another process. For instance, a therapy planning (e.g., radiation, ablation, etc.) station 130 can use the contour to plan a therapy session. Once planned to the satisfaction of the operator, the planned therapy is transferred to a therapy device 132 that implements the planned session. Other stations may use the shaped contour in various other planning processes.

In another embodiment, the MRI patient image with surrogate CT data is used for radiation dose calculation, e.g., using Hounsfield values associated with the landmarks in the patient image during registration.

In another embodiment, the overlay displayed in viewport 118$_3$ is adjustable to weight the MRI image data relative to the CT image data, or vice versa. For instance a slider bar or knob (not shown), which may be mechanical or presented on the display 20 and manipulated with an input device, may be adjusted to vary the weight of the MRI image data or the CT image data. In one example, an operator can adjust the image in viewport 118$_3$ from purely CT image data (as is shown in viewport 118$_1$), through multiple and/or continuous combinations of CT and MRI image data, to purely MRI image data (as is shown in viewport 118$_2$). For example, a ratio of CT image data to MRI image data can be discretely or continuously adjusted from 0:1 to 1:0.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A system that provides electron density information in a magnetic resonance image (MRI) volume, including:
    a memory that stores an atlas including a reference computed tomography (CT) image and a reference MRI image that are co-registered to each other;
    a display that presents a view of a patient MRI image and the reference MRI image;
    a processor that executes an algorithm for associating electron density information from a corresponding landmark in the reference CT image with the selected landmark in the patient MRI image;
    an MRI imaging device that generates the patient MRI image; and
    a nuclear scanner that generates a single photon emission computed tomography (SPECT) image or a positron emission tomography (PET) image of the patient;
    wherein the processor generates attenuation correction data for the patient SPECT or PET image as a function of electron density information from a registered patient MRI image.

2. The system according to claim 1, further including an input device that selects landmarks on the patient MRI image for registration to corresponding landmarks on the reference MRI image.

3. The system according to claim 1, wherein reference CT image is a generic CT image generated from CT images of a plurality of subjects, and the reference MRI image is a generic MRI image generated from MRI images of a plurality of subjects.

4. The system according to claim 1, wherein the reference CT image and the reference MRI image are co-registered by manually registering landmarks in the reference CT image to corresponding landmarks in the reference MRI image and associating electron density information from segmented regions of the reference CT image with a corresponding segments of the reference MRI image.

5. The system according to claim 1, wherein the reference MRI image is deformed to align with the patient MRI image and a radiation therapy plan is generated using the deformed reference MRI image.

6. The system according to claim 1, further including an integrated linear accelerated MRI imaging device that generates the patient MRI image.

7. The system according to claim 1, wherein the atlas includes CT and MRI reference images of differently-sized anatomical structures.

8. The system according to claim 7, wherein the atlas includes CT and MRI reference images of groups of anatomical structures.

9. The system according to claim 1, further including:
a routine for generating the atlas with generic co-registered CT and MRI reference images;
a routine for generating a patient MRI image;
a routine for selecting landmarks in the patient MRI image and registering the selected landmarks to corresponding landmarks in the reference MRI image; and
a routine for retrieving electron density information from the co-registered CT image for the registered patient MRI image.

10. The system according to claim 1, wherein the processor is configured to:
generate generic co-registered CT and MRI reference images from a plurality of respective CT and MRI images;
segment the co-registered CT and MRI reference images to define regions denoting organs or like tissue;
receive patient MRI image data;
receive an input indicating selection of landmarks in the patient MRI image and corresponding landmarks in the reference MRI image;
register the selected landmarks in the patient MRI image to the corresponding landmarks in the reference MRI image; and
retrieve electron density information from a corresponding co-registered CT image segment and associate the retrieved electron density information with the registered patient MRI image segment.

11. A method of providing electron density information for voxels in a magnetic resonance imaging (MRI) image, including:
generating generic co-registered computed tomography (CT) and MRI reference images from a plurality of respective CT and MRI images of a region of interest;
receiving a patient MRI image;
registering the patient MRI image and the reference MRI image;
retrieving electron density information from corresponding segments of the co-registered CT image for the registered patient MRI image;
associating the retrieved electron density information with the registered patient MRI image; and
employing a registered patient MRI image, including the electron density data, to correct for attenuation during at least one of a positron emission tomography (PET) data acquisition and single photon emission computed tomography (SPECT) data acquisition.

12. The method according to claim 11, further including generating a therapy plan using the patient MRI image with retrieved electron density information.

13. The method according to claim 11, further comprising employing an elastic transform to register the patient MRI image to the reference MRI image.

14. The method according to claim 11, wherein the atlas includes a plurality of co-registered CT and MRI reference images of different anatomical structures, CT and MRI reference images of a one or more different-sized anatomical structures, and/or CT and MRI reference images of one or more different combinations of anatomical structures.

15. The method according to claim 11, further including segmenting the co-registered CT and MRI reference images to define regions denoting organs or like tissue.

16. The method according to claim 15, further including receiving an input indicating selection of landmarks in the patient MRI image corresponding to landmarks in the segmented reference MRI image.

17. A processor configured to:
generate generic co-registered computed tomography (CT) and MRI reference images from a plurality of respective CT and MRI images of a region of interest;
receive a patient MRI image;
register the patient MRI image and the reference MRI image;
retrieve electron density information from corresponding segments of the co-registered CT image for the registered patient MRI image; and
associate the retrieved electron density information with the registered patient MRI image.

18. A system including:
a non-transitory computer-readable medium that stores an atlas of co-registered computed tomography (CT) and magnetic resonance imaging (MRI) reference images of anatomical structures, the atlas including:
a plurality of CT and MRI reference images of anatomical structures, generated from scanned images of anatomical structures of one or more subjects, wherein the reference images are co-registered to associate electron density information from voxels in the CT reference images to corresponding voxels in respective MRI reference images;
wherein the non-transitory machine-readable medium stores the plurality of co-registered CT and MRI reference images for recall and manipulation by an operator; and
a display on which is presented to a user a patient MRI image and at least one of the co-registered MRI reference image;
wherein the co-registered MRI reference images comprise electron density data from corresponding CT images that is employed to correct for attenuation during at least one of a positron emission tomography (PET) data acquisition and single photon emission computed tomography (SPECT) data acquisition.

* * * * *